US010709073B2

(12) United States Patent
Millar

(10) Patent No.: US 10,709,073 B2
(45) Date of Patent: Jul. 14, 2020

(54) SYSTEMS AND METHODS FOR COMMUNICATING DATA VIA A PLURALITY OF GROW PODS

(71) Applicant: Grow Solutions Tech LLC, Lehi, UT (US)

(72) Inventor: Gary Bret Millar, Highland, UT (US)

(73) Assignee: Grow Solutions Tech LLC, Vineyard, UT (US)

( * ) Notice: Subject to any disclaimer, the term of this patent is extended or adjusted under 35 U.S.C. 154(b) by 233 days.

(21) Appl. No.: 15/985,019

(22) Filed: May 21, 2018

(65) Prior Publication Data

US 2018/0359956 A1    Dec. 20, 2018

Related U.S. Application Data

(60) Provisional application No. 62/519,329, filed on Jun. 14, 2017, provisional application No. 62/519,330,
(Continued)

(51) Int. Cl.
*A01G 7/00*     (2006.01)
*A01G 9/26*     (2006.01)
(Continued)

(52) U.S. Cl.
CPC .............. *A01G 9/26* (2013.01); *A01G 7/00* (2013.01); *A01G 9/24* (2013.01); *A01G 31/042* (2013.01);
(Continued)

(58) Field of Classification Search
CPC ..................................................... A01G 7/00
(Continued)

(56) References Cited

U.S. PATENT DOCUMENTS

| 6,882,740 | B1 * | 4/2005 | McDonald, Jr. ...... G06T 7/0012 348/89 |
| 7,415,796 | B2 * | 8/2008 | Brusatore ............ A01G 31/047 47/59 R |
| 8,327,580 | B2 * | 12/2012 | Miyahara ................. A01G 9/16 47/60 |
| 8,621,782 | B2 * | 1/2014 | Buck ..................... A01G 31/02 47/58.1 CF |

(Continued)

FOREIGN PATENT DOCUMENTS

| EP | 2870859 A1 | 5/2015 |
| EP | 3197258 A1 | 8/2017 |

(Continued)

OTHER PUBLICATIONS

International Search Report & Written Opinion dated Nov. 12, 2018 for International Application No. PCT/US2018/033811 filed on May 22, 2018.

*Primary Examiner* — Richard T Price, Jr.
(74) *Attorney, Agent, or Firm* — Dinsmore & Shohl LLP

(57) ABSTRACT

Systems and methods for facilitating communication among grow pods are provided. One embodiment of a system includes a remote computing device that includes a memory component that stores logic. The logic may cause the remote computing device to receive a grow recipe that includes actions for a particular grow pod to grow a plant, implement the grow recipe on the particular grow pod; determine an output of the plant in the particular grow pod using the grow recipe, and determine a random adjustment to the grow recipe. In some embodiments, the logic may cause the computing device to determine an output of the plant in the particular grow pod using the random adjustment to the grow recipe and determine whether the random adjustment to the grow recipe resulted in an improvement in output.

20 Claims, 10 Drawing Sheets

Related U.S. Application Data filed on Jun. 14, 2017, provisional application No. 62/519,343, filed on Jun. 14, 2017, provisional application No. 62/519,316, filed on Jun. 14, 2017.

(51) Int. Cl.

| | | |
|---|---|---|
| *G06Q 50/02* | (2012.01) | |
| *G06Q 10/06* | (2012.01) | |
| *A01G 31/04* | (2006.01) | |
| *A01G 9/24* | (2006.01) | |
| *G01N 33/00* | (2006.01) | |
| *H04L 29/08* | (2006.01) | |
| *A01G 9/18* | (2006.01) | |

(52) U.S. Cl.
CPC ... *G01N 33/0098* (2013.01); *G06Q 10/06312* (2013.01); *G06Q 10/06393* (2013.01); *G06Q 50/02* (2013.01); *H04L 67/12* (2013.01); *A01G 9/18* (2013.01)

(58) Field of Classification Search
USPC .............................................. 47/1.3, 1.1, 1.7
See application file for complete search history.

(56) References Cited

U.S. PATENT DOCUMENTS

| | | | |
|---|---|---|---|
| 8,680,014 B2* | 3/2014 | Zhang | A01N 37/42 |
| | | | 252/70 |
| 8,898,955 B2* | 12/2014 | Akay | A01H 3/00 |
| | | | 47/59 S |
| 8,935,881 B2* | 1/2015 | Wolff | A01C 1/025 |
| | | | 47/14 |
| 9,603,316 B1 | 3/2017 | Mansey et al. | |
| 2015/0027040 A1 | 1/2015 | Redden | |
| 2016/0050862 A1 | 2/2016 | Walliser | |
| 2016/0064204 A1 | 3/2016 | Greenberg et al. | |
| 2016/0073573 A1 | 3/2016 | Ethington et al. | |

FOREIGN PATENT DOCUMENTS

| | | |
|---|---|---|
| JP | 2004298069 A | 10/2004 |
| JP | 2005013056 A | 1/2005 |
| JP | 2005013057 A | 1/2005 |
| JP | 4876439 B2 | 2/2012 |
| JP | 2015062395 A | 4/2015 |
| WO | 2017176733 A1 | 10/2017 |

\* cited by examiner

SYSTEMS AND METHODS FOR COMMUNICATING DATA VIA A PLURALITY OF GROW PODS

CROSS REFERENCE

This application claims the benefit of U.S. Provisional Application Ser. No. 62/519,343, filed on Jun. 14, 2017, U.S. Provisional Application Ser. No. 62/519,329, filed on Jun. 14, 2017, U.S. Provisional Application Ser. No. 62/519,330, filed on Jun. 14, 2017, and U.S. Provisional Application Ser. No. 62/519,316, filed on Jun. 14, 2017, which are incorporated by reference in their entireties.

TECHNICAL FIELD

Embodiments described herein generally relate to systems and methods for communicating data via a plurality of grow pods and, more specifically, to systems and methods for facilitating communication among grow pods that may determine improvements to grow recipes and share those improvements in a network of grow pods.

BACKGROUND

While crop growth technologies have advanced over the years, there are still many problems in the farming and crop industry today. As an example, while technological advances have increased efficiency and production of various crops, many factors may affect a harvest, such as weather, disease, infestation, and the like. Additionally, while the United States currently has suitable farmland to adequately provide food for the U.S. population, other countries and future populations may not have enough farmland to provide the appropriate amount of food. Similarly, many current greenhouses are configured to control an environment of a plant; these current solutions are not capable of learning from other greenhouses or performing any other automated processes for growing the plants. As such, a need exists in the industry.

SUMMARY

Systems and methods for facilitating communication among grow pods are provided. One embodiment of a system includes a remote computing device that includes a memory component that stores logic. The logic may cause the remote computing device to receive a grow recipe that includes actions for a particular grow pod to grow a plant, implement the grow recipe on the particular grow pod, determine an output of the plant in the particular grow pod using the grow recipe, and determine a random adjustment to the grow recipe. In some embodiments, the logic may cause the computing device to determine an output of the plant in the particular grow pod using the random adjustment to the grow recipe and determine whether the random adjustment to the grow recipe resulted in an improvement in output.

In some embodiments, the logic may further determine a different grow pod for receiving the random adjustment and the grow recipe, in response to determining that the random adjustment to the grow recipe resulted in an improvement in output and determine features of the different grow pod. In some embodiments, the logic may then alter the grow recipe with the random adjustment to the grow recipe to form a new grow recipe to operate on the different grow pod and implement the new grow recipe on the different grow pod.

In another embodiment, a method for facilitating communication among grow pods is disclosed. The method includes receiving a grow recipe including actions for a particular grow pod to grow a plant, implementing the grow recipe on the particular grow pod, determining an output of the plant in the particular grow pod using the grow recipe, determining a random adjustment to the grow recipe, and determining an output of the plant in the particular grow pod using the random adjustment to the grow recipe. In some embodiments, the method includes determining whether the random adjustment to the grow recipe resulted in an improvement in output. In some embodiments, in response to determining that the random adjustment to the grow recipe did not result in an improvement in output, the method enables storing the random adjustment to the grow recipe. In response to determining that the random adjustment to the grow recipe resulted in an improvement in output, some embodiments of the method enable determining a different grow pod for receiving the random adjustment and the grow recipe, determining features of the different grow pod, altering the grow recipe with the random adjustment to the grow recipe to form a new grow recipe to operate on the different grow pod and sending the new grow recipe to the different grow pod for implementation.

In yet another embodiment, a grow pod for facilitating communication with other grow pods is disclosed. The grow pod includes a pod computing device that includes a memory component that stores logic. The logic may cause the pod computing device to receive a grow recipe which includes actions for the grow pod to grow a plant, implement the grow recipe on the grow pod, determine an output of the plant in the grow pod using the grow recipe, and determine a random adjustment to the grow recipe. In some embodiments, the logic may cause the pod computing device to determine an output of the plant in the grow pod using the random adjustment to the grow recipe and determine whether the random adjustment to the grow recipe resulted in an improvement in output.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Figure 1:
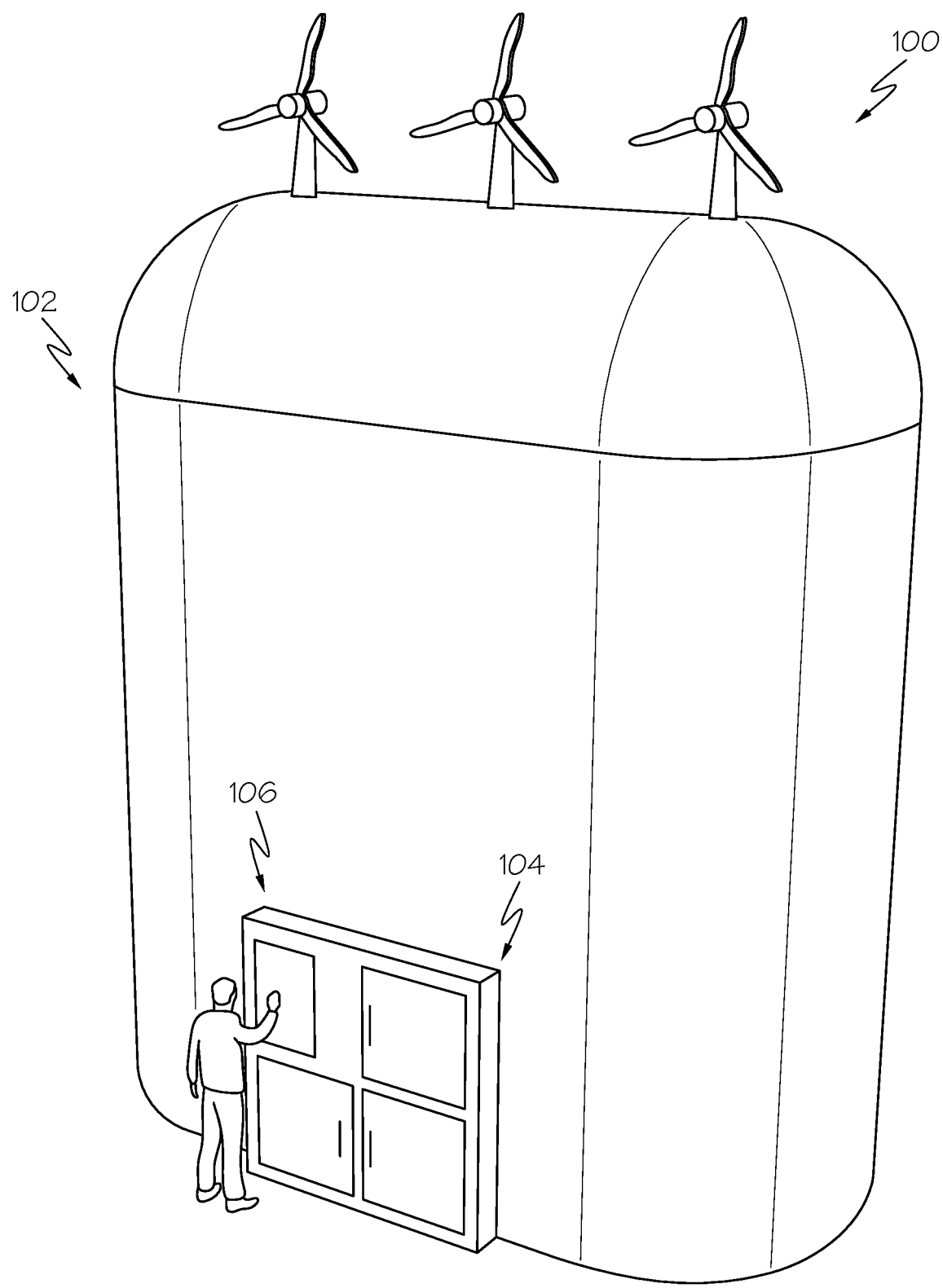
FIG. 1 depicts an assembly line grow pod, according to embodiments described herein.

Embodiments disclosed herein include systems and methods for communicating data via a plurality of grow pods. Some embodiments may be configured to receive an update and/or upgrade of a grow recipe for one or more types of plants. If the update and/or upgrade results in better plant production, better efficiency, etc. that grow pod may communicate the update and/or improvement to a remote computing device for sharing the information with other grow pods.

Specifically, users of a grow pod may receive and/or determine a recipe for growing one or more predetermined plants. The user may personally identify that at least a portion of the recipe that is not providing optimal performance (of the grow pod, of the plant output, and/or related to other performance). The user may make a modification to the recipe, the grow pod, and/or to the plants to improve this performance. As such, embodiments may utilize a computing device of the grow pod and/or a remote computing device to determine whether the adjustment that the user made is unique among all grow pods in the network. If so, the adjustment may be sent to the remote computing device such that someone with similar situation may receive the update to also achieve improved results. As the various grow pods may be different, embodiments are also configured to translate the received recipe designed for a first grow pod to a format for utilization in a second grow pod.

Additionally, some embodiments may be configured to determine a random adjustment to a grow recipe, implement the adjustment, and determine if the adjustment improved the plant output, efficiency of the system, and/or resulted in other benefit. The random adjustment to the grow recipe may be related to altering an amount of air, water, light, airflow, temperature, pressure, or nutrients provided to the plant by an environmental affecter. The environmental affecter may include not only lighting devices, temperature control devices, humidity control devices, pressure control devices, airflow lines, water lines, etc., but also a cart for the grow pod, a seeder component, a harvester component, a watering component, a nutrient component, a sanitizer component and the like. As such, embodiments may be configured to randomly select one or more of the environmental affecters, randomly select a setting, timing, and/or other function of the selected environmental affecter, and/or randomly select the value for that setting. The resultant plant output, grow pod operation, and/or other output may then be determined and compared against a growth profile, operation profile, or the like.

The parameters used to compare output of the plant relate to root growth, stem growth, chlorophyll growth, leaf growth, or fruit output. If the implementation of the random adjustment results in an improved output or result, the adjustment may be shared with another computing device in a network of grow pods and implemented on plants in a different grow pod. If the random adjustment does not result in an improved output, data related to the random adjustment may be stored and noted that the random adjustment was unsuccessful, to prevent (or reduce the likelihood that) that improvement from being utilized again. If the random adjustment proves to be successful, data related to the random adjustment may be formatted and customized for implementation on the different grow pod based on its features.

In some embodiments, a remote computing device may be configured to implement a grow recipe, as well as to facilitate sharing of information with other grow pods. In some embodiments, a pod computing device may be configured to implement a grow recipe, alter the grow recipe, and provide the related data to the remote computing device. However, these embodiments may be configured such that the remote computing device formats the grow recipe and adjustment to a generic grow pod, formats for a particular grow pod, and/or communicates the formatted grow recipe to a different grow pod. In some embodiments, the pod computing device performs both the implementation of the grow recipes as well as the facilitation of sharing of information with other grow pods. Regardless of the distribution of roles, improvements in plant growth, plant output, and operational efficiency of the grow pod can be planned and predicted through the systems and methods described and illustrated herein.

Referring now to the drawings, FIG. 1 depicts an assembly line grow pod 100 according to embodiments described herein. As illustrated, the assembly line grow pod 100 may be a self-contained unit that maintains an environment inside and prevents the external environment for entering. As such, the assembly line grow pod 100 may include an external shell 102 to provide this function. Coupled to the external shell 102 is a control panel 104 with a user input/output device 106, such as a touch screen, monitor, keyboard, mouse, etc. The user input/output device 106 is used to obtain input on desired characteristics of plant output in the grow pod 100. The user input/output device 106 displays as output any measurements and comparisons of the actual output of the plant and the success of a random adjustment to the grow recipe applied to the plant as well as applicability of the random adjustment to other grow pods.

Figure 2A:
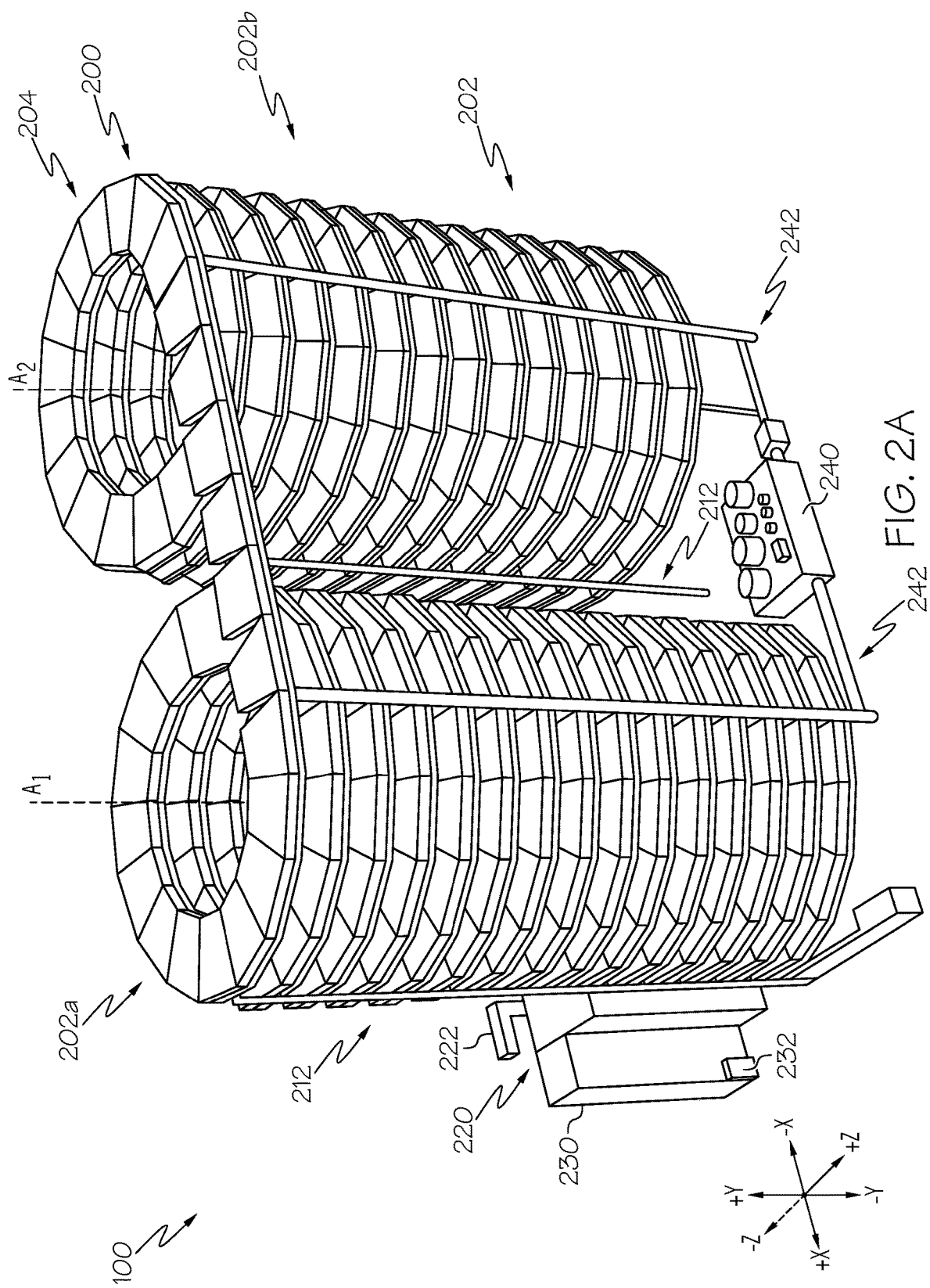
FIGS. 2A-2C depict an operational structure for an assembly line grow pod, according to embodiments described herein.
Figure 2B:
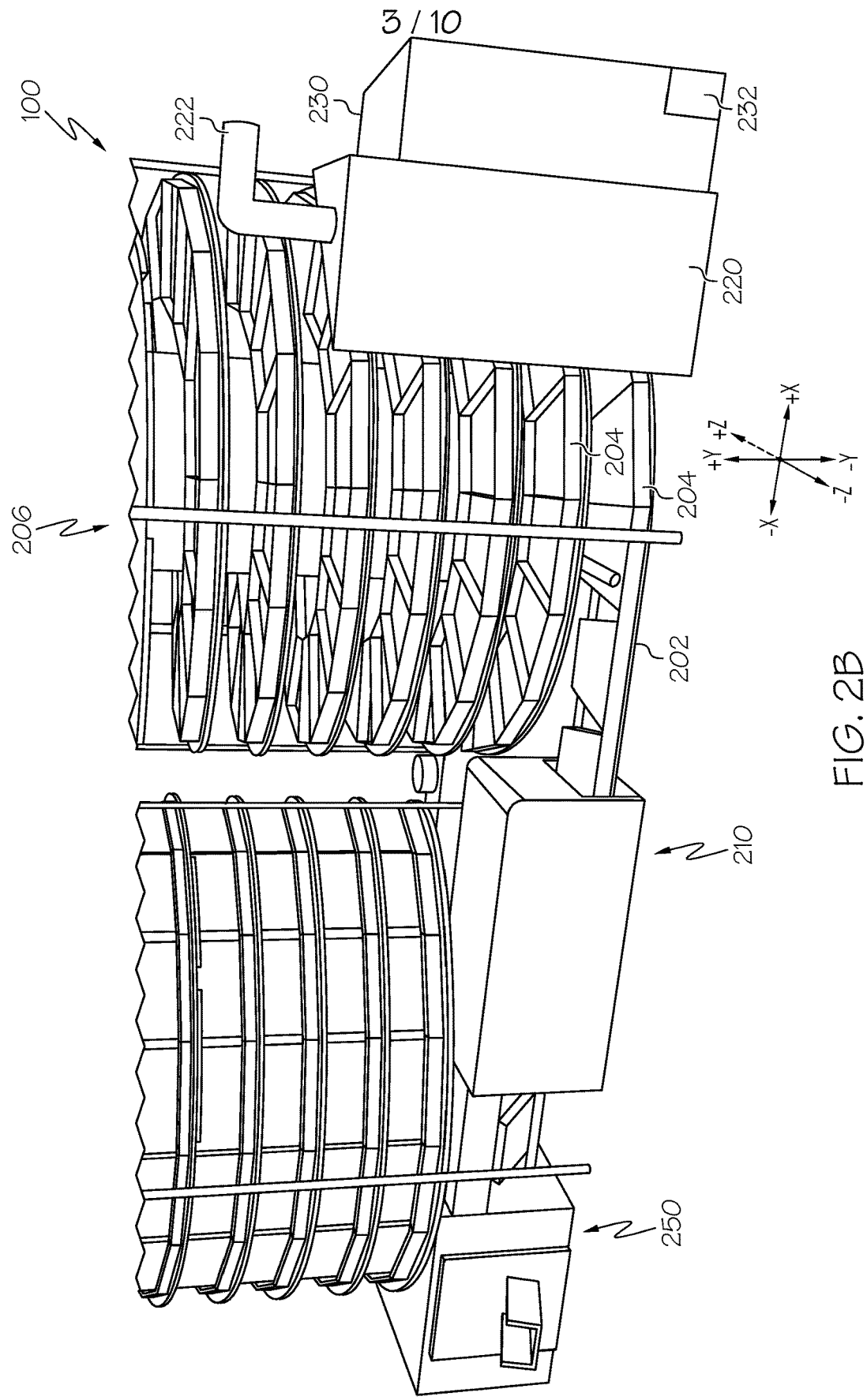
Figure 2C:
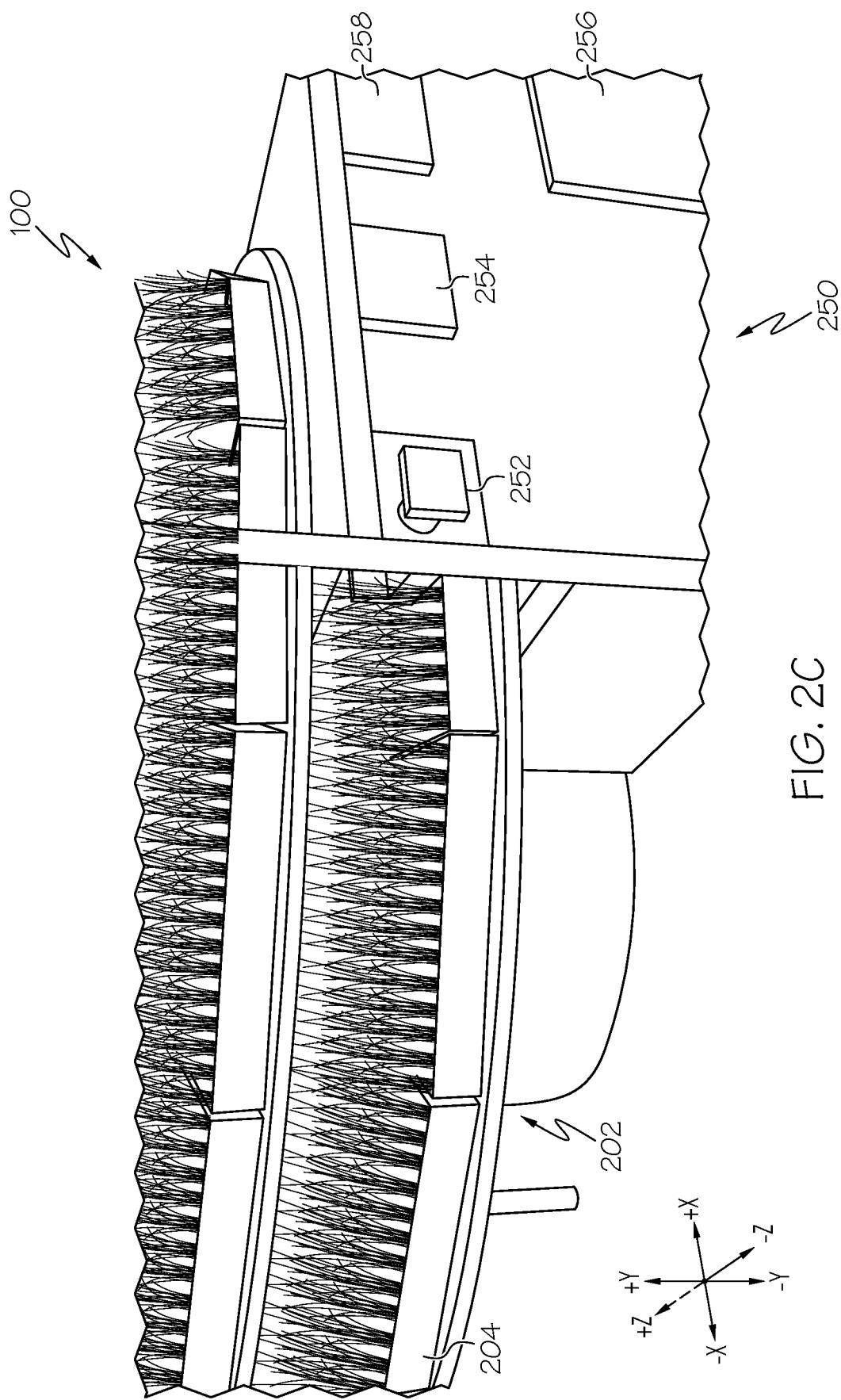

FIGS. 2A-2C depict an operational structure 200 for an assembly line grow pod 100, according to embodiments described herein. As illustrated in FIG. 2A, the operational structure 200 may reside inside the assembly line grow pod 100 and may include a track 202 that holds one or more carts 204. The track 202 may include an ascending portion 202a, a descending portion 202b, and a connection portion 202c in some embodiments. The track 202 may wrap around (in a counterclockwise direction in FIG. 2A, although clockwise or other configurations are also contemplated) a first axis $A_1$ such that the carts 204 can ascend upward in a vertical direction (i.e., in the +y direction of the coordinate axes of FIG. 2A). The connection portion 202c may be relatively level (although this is not a requirement) and is utilized to transfer the carts 204 to the descending portion 202b. The descending portion 202b may be wrapped around a second axis $A_2$ (again in a counterclockwise direction in FIG. 2A) that is substantially parallel to the first axis $A_1$, such that the carts 204 can descend towards the ground level in a vertical direction (i.e., in the -y direction of the coordinate axes of FIG. 2A). While the embodiments of FIGS. 2A and 2B depict an assembly line grow pod 100 that wraps around a plurality of axes, this is merely one example. Any configuration of the assembly line grow pod 100 or a stationary grow pod may be utilized for performing the functionality described herein.

As the carts 204 traverse the track 202 of the assembly line grow pod 100, the plants on the carts 204 are lighted, aired, watered, and provided nutrients. Depending on the particular embodiment, the carts 204 may be individually powered and/or powered collectively. As an example, some embodiments are configured such that each cart 204 includes a motor, which is powered by a connection to the track 202. In these embodiments, the track 202 is electrified to provide power and/or communications to the cart 204. If a cart 204 becomes incapacitated, communication may be sent to other carts 204 to push the incapacitated cart 204. Similarly, some embodiments may include a cart 204 that is powered by battery, such that a battery-charging component may be included in the assembly line grow pod 100. The battery may be used as primary power and/or backup power. As shown in FIGS. 2A and 2B, the assembly line grow pod 100 includes the master controller 230. The master controller 230 may include a pod computing device 232 and/or other hardware for controlling various components of the assembly line grow pod 100. As an example, a water distribution component, a nutrient distribution component, an air distribution component, etc. may be included as part of the master controller 230.

The assembly line grow pod 100 may include a plurality of lighting devices 206 (shown in FIG. 2B) for facilitating plant growth. The lighting devices 206 may be disposed on the track 202 opposite the carts 204, such that the lighting devices 206 direct light waves to the carts 204 (and/or plants) on the portion the track 202 directly below. In some embodiments, the lighting devices 206 are configured to create a plurality of different colors and/or wavelengths of light, depending on the application, the type of plant being grown, and/or other factors. Depending on the particular embodiment, the lighting devices 206 may be stationary and/or movable. As an example, some embodiments may alter the position of the lighting devices 206, based on the plant type, stage of development, grow recipe, and/or other factors. While in some embodiments, light emitting diodes (LEDs) are utilized for this purpose, any lighting device that produces low heat and provides the desired functionality may be utilized.

In some embodiments, the carts 204 are advanced through at least a harvester component 250, a sanitizer component 210 and a seeder component 220 of the assembly line grow pod 100 along the track 202 (shown in FIG. 2B). The assembly line grow pod 100 may detect a growth and/or fruit output of a plant and may determine when harvesting is warranted. If harvesting is warranted prior to the cart 204 reaching the harvester component 250, modifications to a grow recipe may be made for that particular cart 204 until the cart 204 reaches the harvester component 250. Conversely, if a cart 204 reaches the harvester component 250 and it has been determined that the plants in the cart 204 are not ready for harvesting, the assembly line grow pod 100 may commission that cart 204 for another lap. This additional lap may include a different dosing of light, water, nutrients, etc. and the speed of the cart 204 could change, based on the development of the plants on the cart 204. If it is determined that the plants on the cart 204 are ready for harvesting, the harvester component 250 harvests the plants on the cart 204 by cutting, chopping, dumping, juicing, and/or otherwise processing. In some embodiments, the harvester component 250 includes a camera 252 for capturing images of the plant, leaves and fruits. The harvester component 250 may also include a first sensor 254 for measuring stem growth, a second sensor 256 for measuring root growth, and a third sensor 258 for measuring content of chlorophyll in the leaves of the plant. In some embodiments, the first sensor 254 may be a stem scanner configured to capture high-resolution digital close-up images of the stem system of the plant. In some embodiments, the second sensor 256 may be a root scanner configured to capture non-destructive, high-resolution, digital images of the root system of the plant. In some embodiments, the third sensor 258 may be a chlorophyll meter.

In some embodiments, the harvester component 250 (shown in FIGS. 2B and 2C) may simply cut the plants at a predetermined height for harvesting. In some embodiments, the cart 204 may be overturned to remove the plants from the tray and into a processing container for chopping, mashing, juicing, etc. Since many embodiments of the assembly line grow pod 100 do not use soil, minimal (or no) washing of the plants may be necessary prior to processing. Similarly, some embodiments may be configured to automatically separate fruit from the plant, such as via shaking, combing, etc. If the remaining plant material may be reused to grow additional fruit, the cart 204 may keep the remaining plant and return to the growing portion of the assembly line grow pod 100. If the plant material is not to be reused to grow additional fruit, it may be discarded or processed, as appropriate. Depending on the embodiment, the final product may include a powder form of the plant, a chopped form of the plant, and/or other form of the plant. Once the plants are harvested in the harvester component 250, the carts 204 pass through the sanitizer component 210 for cleaning.

The sanitizer component 210 (shown in FIG. 2B) is operatively connected in the assembly line grow pod 100 between the harvester component 250 and the seeder component 220 (shown in FIG. 2B). The sanitizer component 210 receives the cart 204 on the track 202 from the harvester component 250. However, the sanitizer component 210 may also receive the cart 204 on an auxiliary track (not shown) that bypasses the harvester component 250. Such an auxiliary track may be utilized for a cart 204 that bypasses the harvester component 250 because the cart 204 includes seeds/plants that have been determined to be dead, contaminated, unsalvageable, etc. The sanitizer component 210 is utilized to remove any particulate, plant material, unused plant matter, water, contaminants, etc. that may remain in the cart 204 as well as to clean and sanitize the cart 204. As such, the sanitizer component 210 implements any of a plurality of different washing mechanisms, such as high pressure water, high temperature water, and/or other solutions for cleaning the cart 204. Once cleaned, the carts 204 advance to the seeder component 220, which determines if seeding is required and if so, begins the process of seeding.

A seeder component 220 (shown in FIG. 2B) is coupled to the master controller 230. The seeder component 220 may be configured to seed one or more carts 204 as the carts 204 pass the seeder in the assembly line. A seeder head 222 may facilitate seeding of the cart 204. Depending on the particular embodiment, each cart 204 may include a single section for receiving a plurality of seeds, or multiple sections for receiving individual seeds in different sections. In some embodiments where the cart 204 has a single section as shown in FIG. 2B, the seeder head 222 is an arm that spreads a layer of seed across a width of the cart 204. The seeder component 220 may detect presence of the respective cart 204 and may begin laying seed across an area of the single section. The seeds may be laid out according to a desired depth of seed, a desired number of seeds, a desired surface area of seeds, and/or according to other criteria. The seeds may be pre-treated with nutrients and/or anti-buoyancy agents (such as water) as these embodiments may not utilize soil to grow the seeds and thus might need to be submerged. In some embodiments where the cart 204 has multiple sections, the seeder head 222 is configured to place one or more seeds individually in the different sections. The seeds may be distributed on the sections of the cart 204 according to a desired number of seeds, a desired area the seeds should cover, a desired depth of seeds, etc.

A watering component 240 (shown in FIG. 2A) may be coupled to one or more water lines 242, which distribute water and/or nutrients to one or more trays at predetermined areas of the assembly line grow pod 100. In some embodiments, seeds may be sprayed to reduce buoyancy and then flooded. Water is stored in one or more fluid tanks (not shown) which are fluidly connected to the sanitizer component 210 and/or the watering component by the water lines 242. The fluid tanks (i) provide water, nutrients, and/or other fluids for plant growth, (ii) provide fluid to the sanitizer component 210, (iii) collect used water from plant watering and/or used water from washing/sanitizing the carts 204, and/or (iv) store water and/or other fluids during a water recycling process. In some embodiments, water may be transferred between the fluid tanks while undergoing water reconditioning or recycling processes. The recollection and recycling of water allows the assembly line grow pod 100 to efficiently use water and produce little or no wastewater. For example, without limitation, the used water may be recycled through the steps of coagulation, sedimentation, filtration, disinfection and storage. Additionally, water usage and consumption may be monitored, such that at subsequent watering stations, this data may be utilized to determine an amount of water to apply to a seed at that time.

Airflow lines 212 are coupled to the assembly line grow pod 100 for distributing airflow at predetermined areas therein. Specifically, the master controller 230 may include and/or be coupled to one or more components that delivers airflow for temperature control, pressure, carbon dioxide control, oxygen control, nitrogen control, etc.

A number of environmental sensors (not shown) may be placed at various locations throughout the grow pod 100 for measuring environmental conditions such as air, water, light, airflow, temperature, pressure, nutrients in soil etc. For example, a pitot tube located at various points in the grow pod 100 may be used to measure airflow. A moisture sensor and a pH meter located on or under the tracks 202 of the grow pod 100 may be used to measure water content and acidity of the soil respectively. A soil test kit may be used to evaluate the nutrient content of the soil by checking the levels of nitrogen, phosphorus, and potassium in the soil. A photometer may be used to measure the intensity of the light incident on the plants, while a camera may be used to capture images of the color of light incident on the plants. Finally, temperature sensors and pressure sensors positioned throughout the grow pod 100 may be used to determine the temperature and pressure conditions respectively. The environmental sensors in the grow pod may be controlled by a user through a user computing device 352 or automatically controlled by a remote computing device 354 or the pod computing device 232 in the master controller 230. Additionally, the grow pod 100 may also have a number of operational sensors such as, but not limited to, speed sensors, timers etc. disposed through the various components and track 202 of the grow pod 100.

Figure 3:
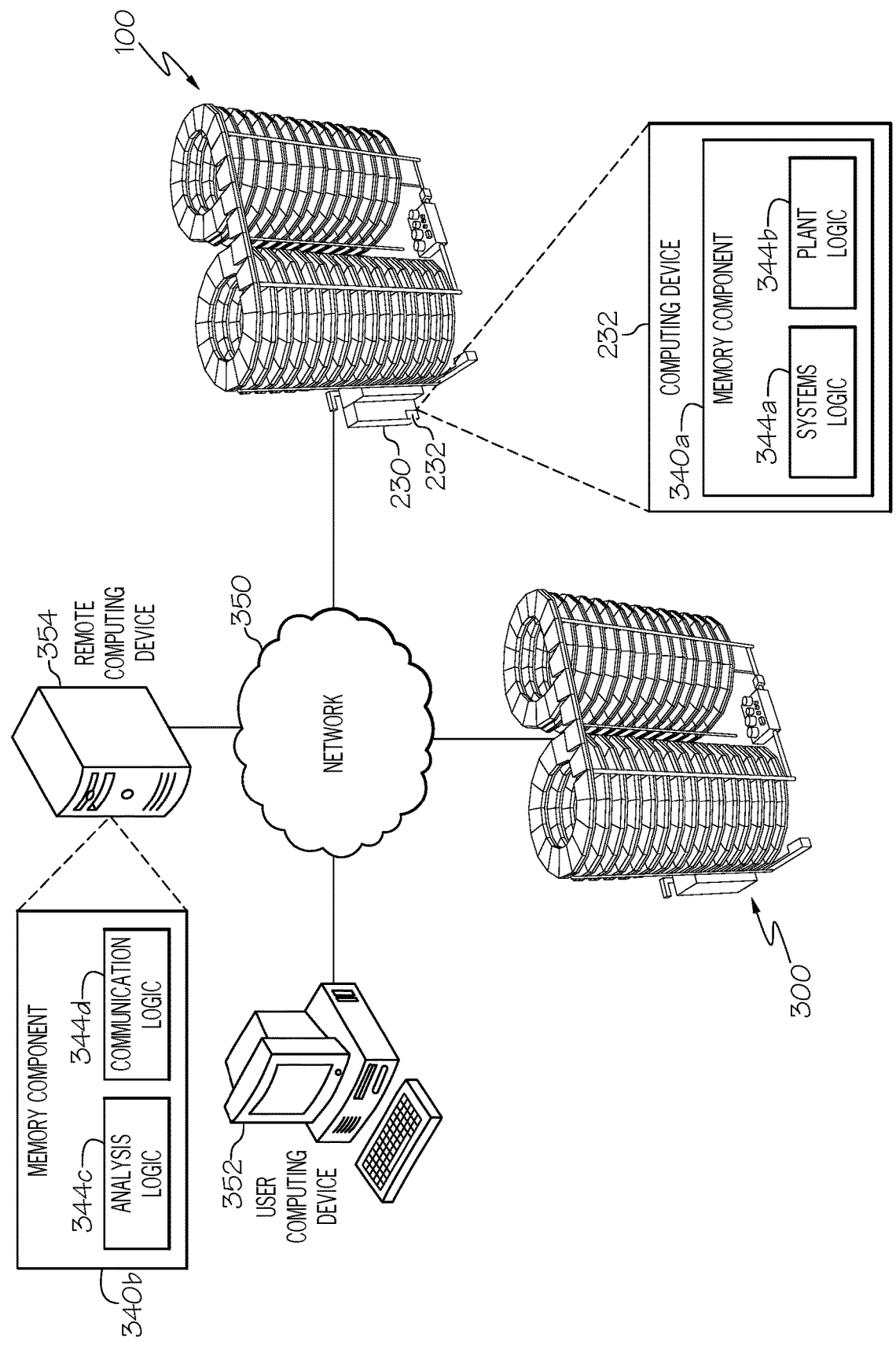
FIG. 3 schematically depicts a computing environment for an assembly line grow pod, according to embodiments described herein.

FIG. 3 depicts a computing environment for the assembly line grow pod 100, according to embodiments described herein. As described above, the assembly line grow pod 100 may include the master controller 230, which may include the pod computing device 232. The pod computing device 232 may include a memory component 340*a*, which stores systems logic 344*a* and plant logic 344*b*. The systems logic 344*a* may monitor and control operations of one or more of the components of the assembly line grow pod 100 and may provide one or more of the user interfaces described herein. As an example, the systems logic 344*a* may receive and/or determine updates, upgrades or adjustments to current grow recipes, receive new grow recipes, and/or otherwise control operations of the assembly line grow pod 100. The plant logic 344*b* may be configured to determine plant growth and may facilitate implementation of the grow recipe via the systems logic 344*a*.

Additionally, the assembly line grow pod 100 is coupled to a network 350. The network 350 may include the internet or other wide area network, a local network, such as a local area network, a near field network, such as Bluetooth or a near field communication (NFC) network. The network 350 is also coupled to the user computing device 352, the remote computing device 354, and/or another assembly line grow pod 300 having a pod computing device, similar to the pod computing device 232. The user computing device 352 may be a personal computer, laptop, mobile device, tablet, server, etc. and may be utilized as an interface with a user through the user input/output device 106. In some embodiments, the remote computing device 354 may send a grow recipe to the pod computing device 232 for implementation by the assembly line grow pod 100. The assembly line grow pod 100 may then send notification to a user of the user computing device 352.

The remote computing device 354 may be configured as a server, personal computer, tablet, mobile device, etc. and may be utilized for machine to machine communications. Accordingly, the remote computing device 354 may include a memory component 340*b*. The memory component 340*b* may store analysis logic 344*c* and communication logic 344*d*. The analysis logic 344*c* may be configured to receive a grow recipe, determine updates, upgrades, and/or adjustments to a grow recipe and determine differences between the grow recipe received and the current grow recipe that is stored by the remote computing device 354. The remote computing device 354 may alter the stored grow recipe and/or save the received grow recipe for communicating the update, upgrade or adjustment to another assembly line grow pod 300 via the communication logic 344*d*.

Figure 4:
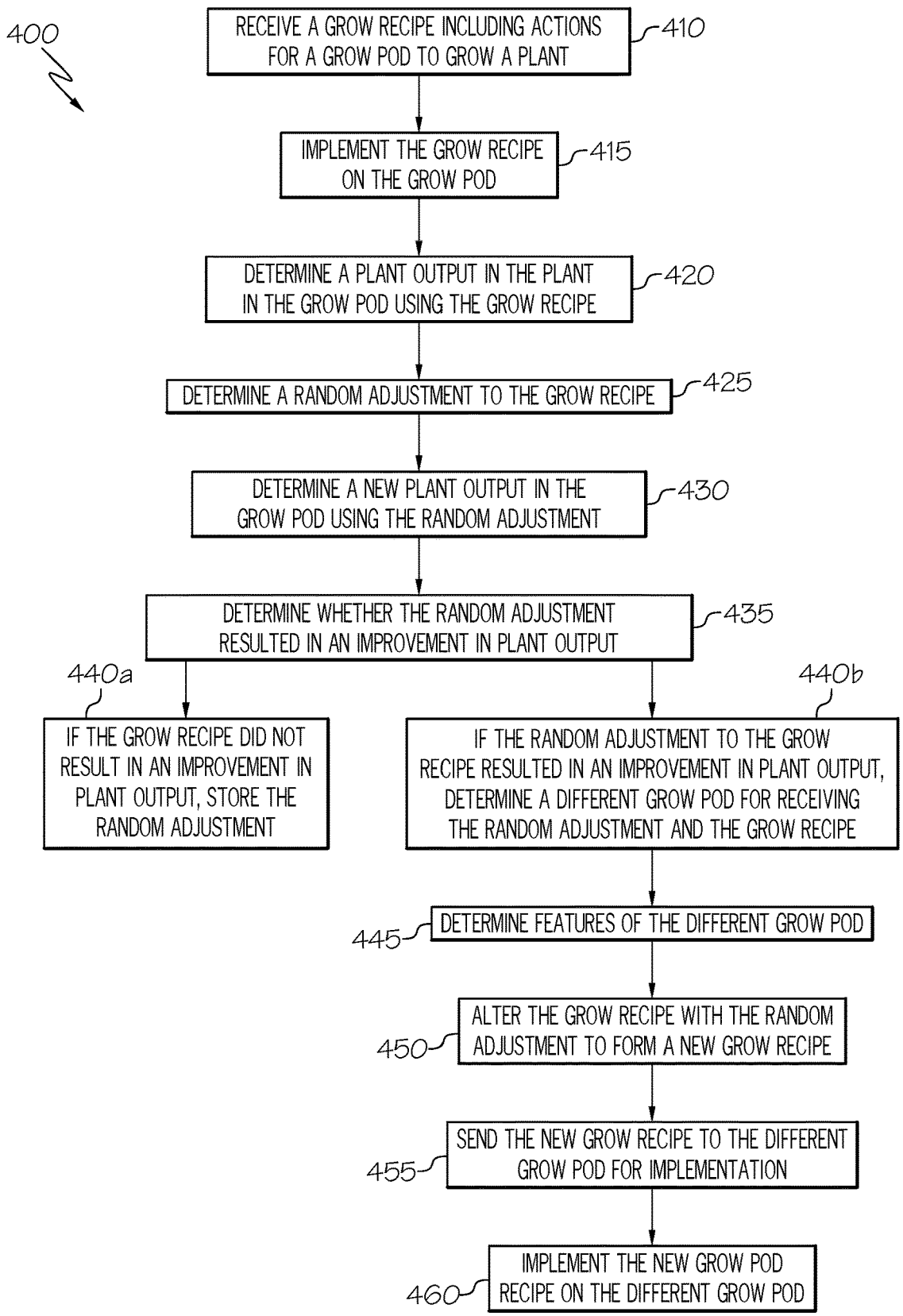
FIG. 4 depicts a flow diagram for facilitating communication among grow pods, according to embodiments described herein.

FIG. 4 depicts a flow diagram of a method 400 for facilitating communication among grow pods, according to embodiments described herein. The method 400 begins in block 410, where a grow recipe lists actions for a particular grow pod to grow a plant is received. The particular grow pod includes a plurality of environment affecters. As discussed above, the environment affecters may include a lighting device, a temperature control device, a humidity control device, a pressure control device, airflow lines, water lines, a watering component, a nutrient component, a cart for the grow pod, a harvester component, a seeder component, a sanitizer components, and/or other devices for affecting the environment and/or operation of the grow pod. In block 415, the grow recipe is implemented on the particular grow pod. In block 420, an output of the plant in the particular grow pod using the grow recipe is determined. In some embodiments, the output could be in the form of root growth, stem growth, chlorophyll growth, leaf growth, or fruit output.

In block 425, a random adjustment to the grow recipe is determined. The random adjustment is performed by activating at least one of the plurality of environment affecters discussed above. The random adjustment may include altering an amount of air, water, light, airflow, temperature, pressure, or nutrients provided to the plant.

In block 430, a new output of the plant in the particular grow pod using the random adjustment in the grow recipe is determined. In block 435, the method 400 enables a determination of whether the random adjustment to the grow recipe resulted in an improvement in the output of the plant. Such a determination is informed by comparing a predetermined growth profile for the plant in the particular grow pod that includes a desired output for a plurality of components of the plant with an actual output of the plant. In some embodiments, the desired output relates to improvements in plant growth, plant output, and/or operational efficiency of the grow pod.

In block 440*a*, the random adjustment to the grow recipe is stored in response to determining that the random adjustment to the grow recipe did not result in an improvement in the output. The random adjustment to the grow recipe is then compared to a previously-stored random adjustment to the grow recipe that did not result in an improvement in the output of the plant. If the random adjustment to the grow recipe is determined to be similar to the previously-stored random adjustment to the grow recipe, the random adjustment to the grow recipe is discarded and another random adjustment to the grow recipe is identified. In block 440*b*, a different grow pod for receiving the random adjustment and the grow recipe is determined, in response to determining that the random adjustment to the grow recipe resulted in an improvement in the output.

In block 445, the features of the different grow pod selected for implementing the grow recipe and the random adjustment are determined. In block 450, the grow recipe is altered with the random adjustment to form a new grow recipe to operate on the different grow pod. In block 455, the new grow recipe is sent to the different grow pod for implementation. The different grow pod receives the new grow recipe and determines if the new grow recipe is formatted for implementation. If the new grow recipe is not formatted for implementation in the different grow pod, the new grow recipe is formatted to operate on the different grow pod. Finally, in block 460, the new grow recipe is implemented on the different grow pod.

In some embodiments, a pod computing device in the master controller of the grow pod performs blocks 410, 415, 420, 425, 430, 435 before the results from block 435 are sent to a remote computing device, which then performs blocks 440*a* or 440*b*, 445, 450, 455 and 460. In another set of embodiments, the pod computing device performs blocks 410, 415, 420, 425, 430, 435, 440*a* or 440*b*, 445, 450, 455 and 460. In yet another set of embodiments, the remote computing device performs blocks 410, 415, 420, 425, 430, 435, 440*a* or 440*b*, 445, 450, 455 and 460.

Figure 5:
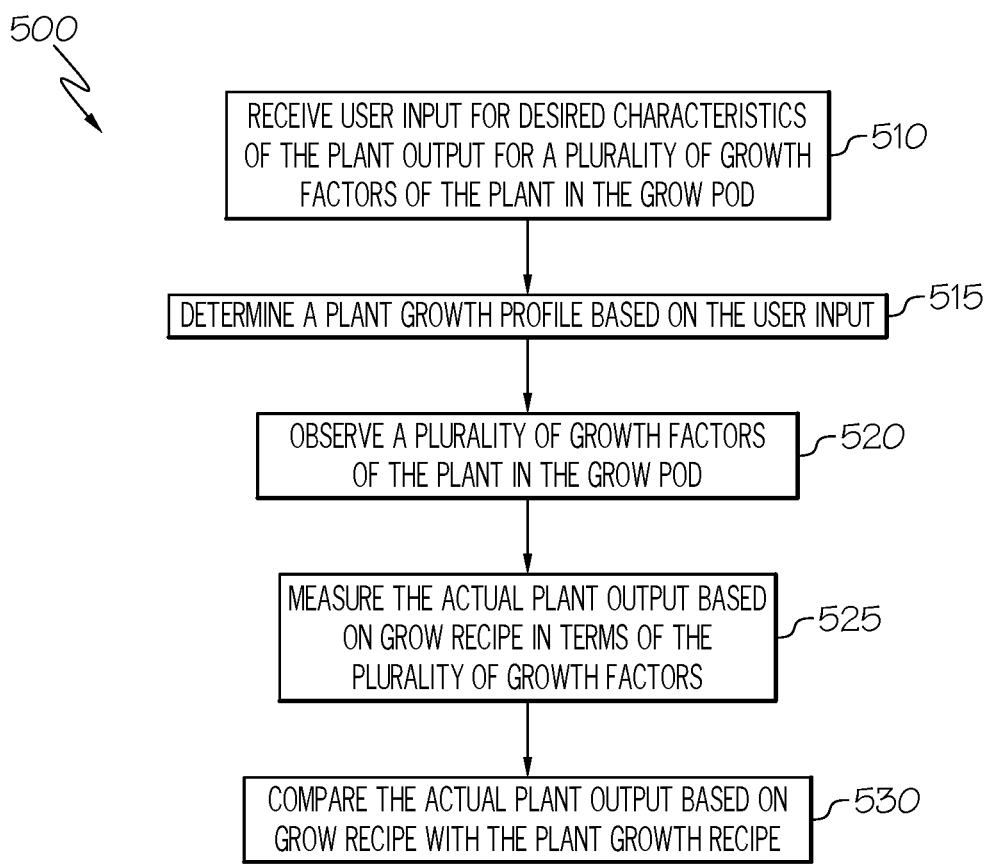
FIG. 5 depicts a flow diagram for determining a plant output based on a grow recipe, according to embodiments described herein.

FIG. 5 depicts a flow diagram of a method 500 for determining a plant output based on a grow recipe as required in blocks 420 and 430 in FIG. 4, according to embodiments described herein. In block 510, a user input is received for a plant in the grow pod in terms of the desired characteristics of the output sought by the user and may take the form of a desired amount of a plurality of the growth factors—root growth, stem growth, chlorophyll growth, leaf growth, or fruit output. For example, the user input may take the form of a desired length of stem, number of fruits harvested, etc. In block 515, the desired characteristics are interpreted and processed to determine a growth profile for the plant in the grow pod. The growth profile is expressed in terms of the growth factors. In block 520, the plurality of growth factors of the plant in the grow pod are observed by a number of sensors. The sensors may be positioned in the harvester component of the grow pod to obtain accurate data on the plurality of growth factors. For example, a camera may capture images of leaves of the plants or the number of fruits ready for harvesting. A first sensor such as, but not limited to, a stem scanner may be used to determine the development of the stem system, as discussed above. A second sensor such as, but not limited to, a root scanner may be used to determine the development of the root system of the plant, as discussed above. A chlorophyll meter may be used to determine the content of chlorophyll.

In block 525, an actual output of the plant is measured in terms of one or more of the plurality of growth factors. The actual output of the plant is an outcome of a grow recipe implemented in the grow pod. The grow recipe includes instructions for undertaking a sequence of actions in the grow pod to maintain the plants and deliver produce. In block 530, the actual plant output based on the grow recipe is compared with the growth profile for the plant, as desired by the user. This helps determine how closely the actual plant output matches the growth profile and whether any further adjustment is necessary. The data on actual plant output is displayed on a user input/output device for notification and any subsequent use.

In some embodiments, blocks 510, 515, 520, 525 and 530 may be performed by a remote computing device or a pod computing device. The remote computing device or the pod computing device may be communicatively connected to a user computing device operated by an external user of the grow pod. The user computing device may have a user interface through which a user may input desired characteristics of output of plants in the grow pods.

Figure 6:
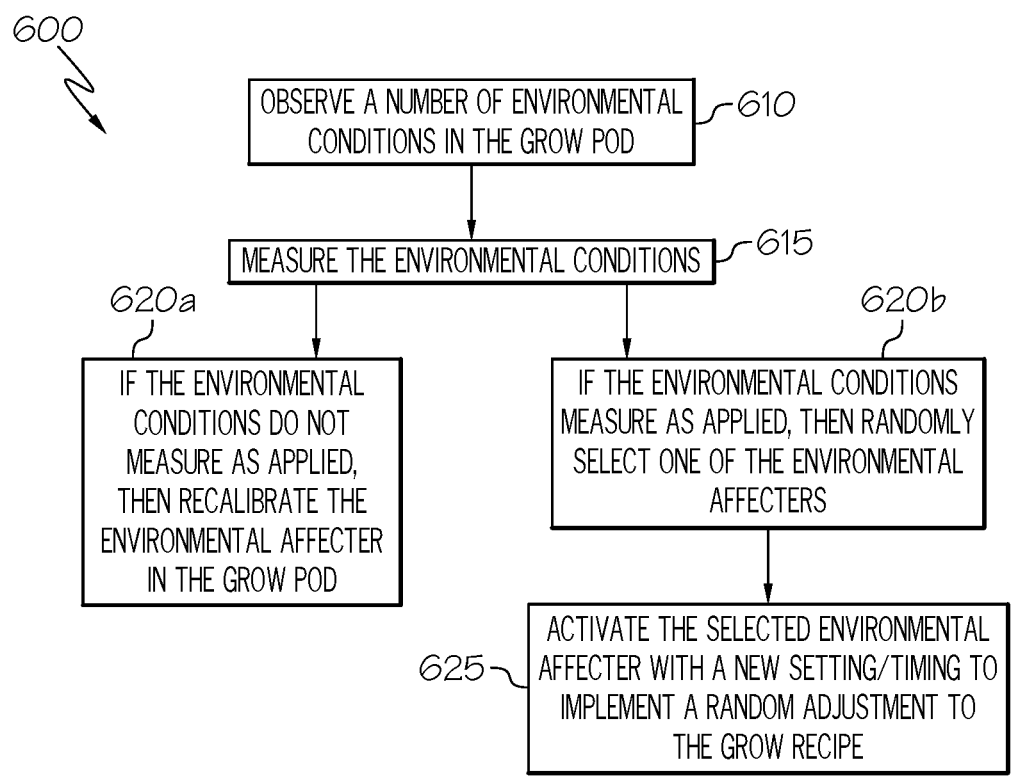
FIG. 6 depicts a flow diagram for determining a random adjustment for a grow recipe, according to embodiments described herein.

FIG. 6 depicts a flow diagram of a method 600 for determining a random adjustment for a grow recipe as described in block 425 in FIG. 4, according to embodiments described herein. In block 610, a number of operational conditions are observed in the grow pod. The operational conditions include air, water, light, airflow, temperature, pressure and nutrients provided to the plant, as well as speed of the carts, cleaning time, seeding time and cycle, etc. In block 615, the operational conditions are measured using the environmental sensors, described above, as well as other operational sensors such as speed sensors, timers, etc. disposed throughout the components and tracks of the grow pod.

In block 620*a*, if the operational conditions do not measure as applied, the environmental affecters may be recalibrated. This allows the environmental conditions to correspond with those in the grow recipe. In block 620*b*, if the environmental conditions measure as applied, one or more of the environmental affecters, as described above, are selected randomly and activated with a new setting/timing by the master controller to implement a random adjustment to the grow recipe.

The random adjustment could be directed to alter an amount of air, water, light, airflow, temperature, pressure or nutrients provided to the plant. The random adjustment could also be directed to alter the speed of the cart, cleaning time, seeding time and cycle. The random adjustment thus affects the conditions that the plant is exposed to and ultimately affects plant growth and output as well as operation of the grow pod. For example, if the random adjustment is directed to slowing the speed of the cart, the plant may get prolonged exposure to air, water or light which aids plant growth, while also reducing wear on the wheels of the cart. The data on random adjustment is displayed on a user input/output device for notification and any subsequent use.

Figure 7A:
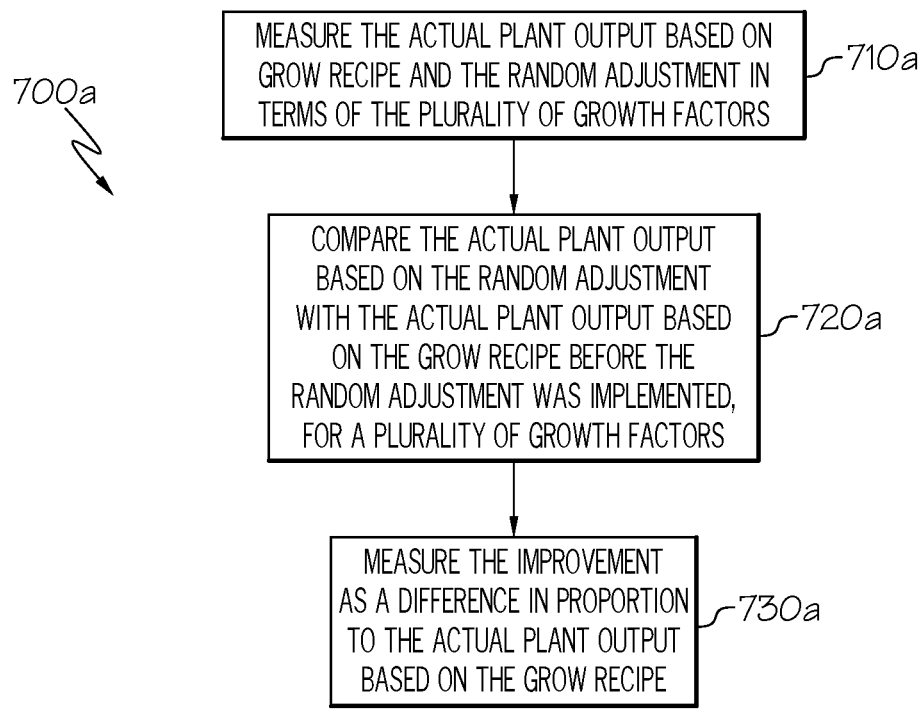
FIGS. 7A-7B depict flow diagrams for determining whether a random adjustment to a grow recipe resulted in an improvement in plant output, according to embodiments described herein.
Figure 7B:
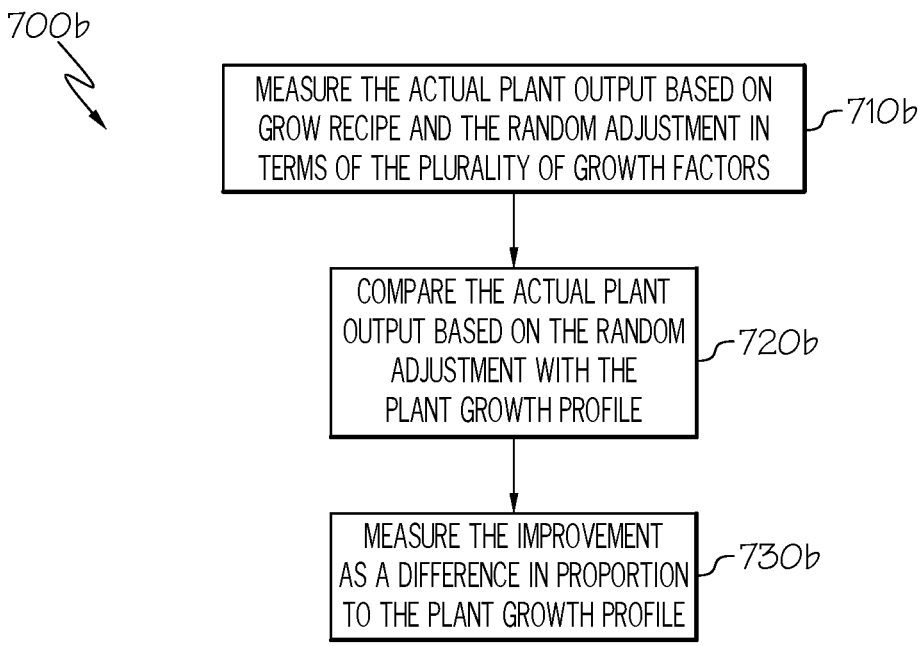

FIGS. 7A-7B depict flow diagrams for determining whether a random adjustment to a grow recipe resulted in an improvement in plant output as described in block 435 in FIG. 4, according to embodiments described herein. FIG. 7A depicts a flow diagram of a method 700a for determining whether the random adjustment resulted in an improvement in plant growth or plant output. In block 710a, the actual output of the plant is measured based on the random adjustment to the grow recipe using the block diagram of FIG. 5. The actual output of the plant is an outcome of a grow recipe implemented in the grow pod and the random adjustment applied to the grow recipe. The measurement may be determined in terms of one or more of the plurality of growth factors such as root growth, stem growth, chlorophyll growth, leaf growth, or fruit output. In block 720a, the actual output of the plant based on the random adjustment to the grow recipe is compared with the actual output of the plant based on the grow recipe before the random adjustment was implemented, also as determined by the block diagram in FIG. 5. This indicates if there has been an improvement in plant growth or plant output. In block 730a, the improvement is measured as a difference in proportion to the actual output of the plant based on the grow recipe, which indicates a first degree of success of the random adjustment.

FIG. 7B depicts a flow diagram of a method 700b for determining whether the random adjustment resulted in an improvement geared towards achieving the desired growth profile and/or grow pod efficiency. In block 710b, the actual output of the plant is measured based on the random adjustment to the grow recipe using the block diagram of FIG. 5. The actual output of the plant is an outcome of a grow recipe implemented in the grow pod and the random adjustment applied to the grow recipe. The measurement may be determined in terms of one or more of the plurality of growth factors such as root growth, stem growth, chlorophyll growth, leaf growth, or fruit output. In block 720b, the actual output of the plant based on the random adjustment to the grow recipe is compared with the plant growth profile obtained through user input in FIG. 5. This indicates if the improvement is geared towards achieving the desired growth profile and/or grow pod efficiency. In block 730b, the improvement is measured as a difference in proportion to the plant growth profile, which indicates a second degree of success of the random adjustment. The comparisons and measurements are then displayed on a user input/output device for notification and any subsequent use.

Figure 8:
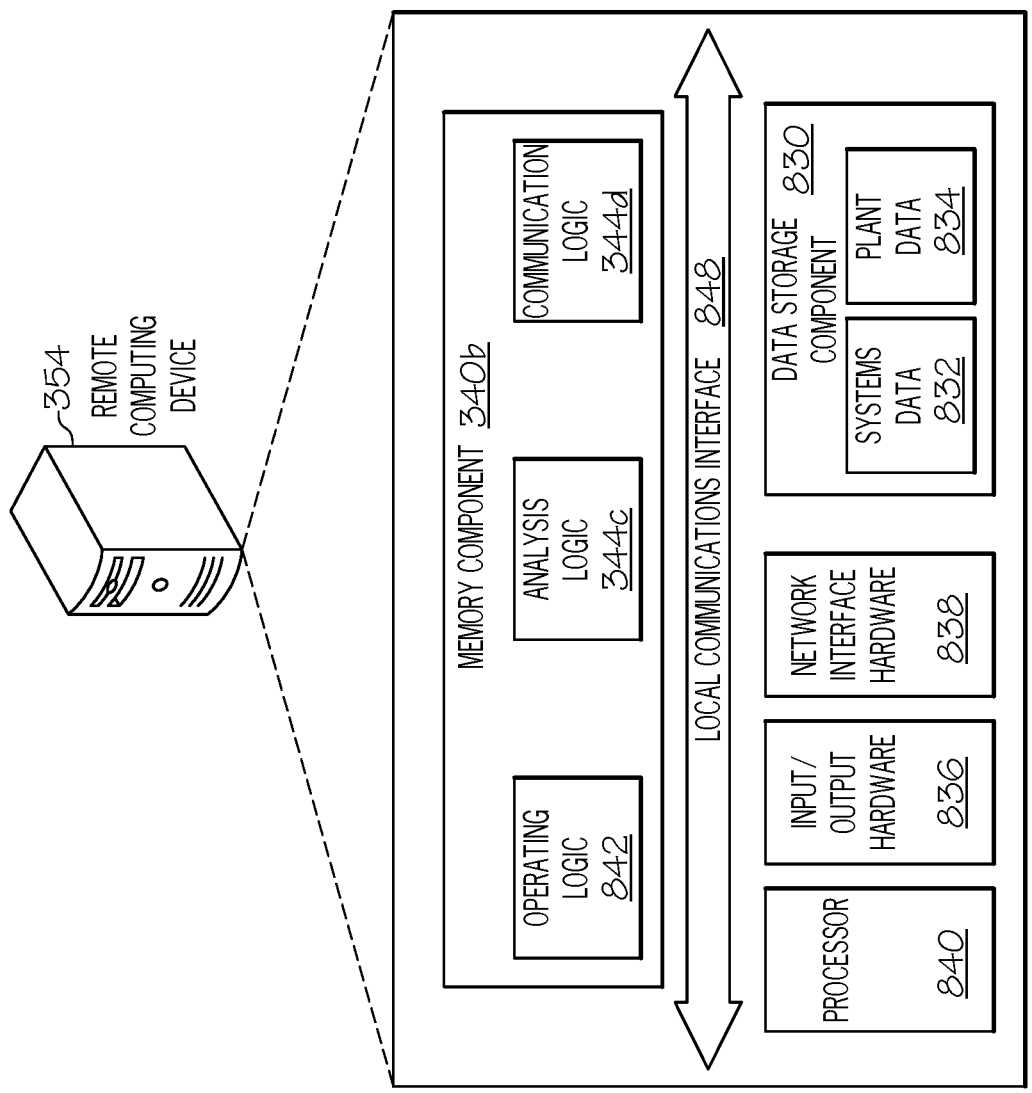
FIG. 8 schematically depicts a remote computing device for communicating data via a plurality of grow pods, according to embodiments described herein.

FIG. 8 shows a block diagram of illustrative hardware components of the remote computing device 354 for communicating data via a plurality of grow pods, according to embodiments described herein. As discussed above, the remote computing device 354 includes a memory component 340b, a processor 840, input/output hardware 836, network interface hardware 838, and a data storage component 830 (which stores systems data 832, plant data 834, and/or other data). Each of the components of the remote computing device 354 may be communicatively coupled to a local communications interface 848. The local communications interface 848 is generally not limited by the present disclosure and may be implemented as a bus or other communications interface to facilitate communication among the components of the master controller 230 coupled thereto.

The memory component 340b may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), Blu-Ray discs, and/or other types of non-transitory computer-readable mediums. Depending on the particular embodiment, these non-transitory computer-readable mediums may reside within or outside the remote computing device 354. The memory component 340b may store, for example, operating logic 842, analysis logic 344c and communication logic 344d. The operating logic 842, the analysis logic 344c and the communication logic 344d may each include a plurality of different pieces of logic, each of which may be embodied as a computer program, firmware, and/or hardware, as an example.

The operating logic 842 may include an operating system and/or other software for managing components of the remote computing device 354. As discussed above, the analysis logic 344c and the communication logic 344d may reside in the memory component 340b and may be configured to perform the functionality, as described above. In some embodiments, the analysis logic 344c and the communication logic 344d may reside on different computing devices. As an example, one or more of the functionalities and/or components described herein may be provided by the user computing device 352 and/or pod computing device 232. While the remote computing device 354 is illustrated with the analysis logic 344c and the communication logic 344d as separate logical components, this is only an example. In some embodiments, a single piece of logic (and/or or several linked modules) may cause the remote computing device 354 to provide the described functionality.

The processor 840 may include any processing component operable to receive and execute instructions (such as from the data storage component 830 and/or the memory component 340b). Illustrative examples of the processor 840 include, but are not limited to, a computer processing unit (CPU), a many integrated core (MIC) processing device, an accelerated processing unit (APU), a digital signal processor (DSP). In some embodiments, the processor 840 may be a plurality of components that function together to provide processing capabilities, such as integrated circuits (including field programmable gate arrays (FPGA)) and the like.

The input/output hardware 836 may include and/or be configured to interface with microphones, speakers, a display, and/or other hardware. That is, the input/output hardware 836 may interface with hardware that provides a user interface or the like. For example, a user interface may be provided to a user for the purposes of adjusting settings, viewing a status, and/or the like.

The network interface hardware 838 may include and/or be configured for communicating with any wired or wireless networking hardware, including an antenna, a modem, LAN port, wireless fidelity (Wi-Fi) card, WiMax card, ZigBee card, Bluetooth chip, USB card, mobile communications hardware, and/or other hardware for communicating with other networks and/or devices. From this connection, communication may be facilitated between the remote computing device 354 and other computing devices, such as user computing devices and/or the pod computing device 232 in the assembly line grow pod 300 (FIG. 3).

The data storage component 830 may generally be any medium that stores digital data, such as, for example, a hard disk drive, a solid state drive (SSD), a compact disc (CD), a digital versatile disc (DVD), a Blu-Ray disc, and/or the like. It should be understood that the data storage component 830 may reside local to and/or remote from the remote computing device 354 and may be configured to store one or more pieces of data and selectively provide access to the one or more pieces of data.

It should be understood that while the components in FIG. 4 are illustrated as residing within the remote computing device 354, this is merely an example. In some embodiments, one or more of the components may reside external to the remote computing device 354. It should also be understood that, while the remote computing device 354 is illustrated as a single device, this is also merely an example. That is, the remote computing device 354 may represent a plurality of devices that are communicatively coupled to one another and provide the functionality described herein.

Additionally, while the remote computing device 354 is illustrated with the various logic components (e.g., the operating logic 842, the analysis logic 344c and the communication logic 344d) and data components (e.g., the systems data 832 and the plant data 834) as separate components, this is also an example. In some embodiments, a single piece of logic (and/or a plurality of linked modules) and/or a single data component (and/or a plurality of linked modules) may also cause the remote computing device 354 to provide the functionality described herein.

As illustrated above, various embodiments for communicating with a plurality of grow pods are disclosed. As illustrated above, these embodiments may allow for sharing of grow recipe knowledge to improve overall plant growth and system efficiency.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for communication with a plurality of grow pods. It should also be understood that these embodiments are merely exemplary and are not intended to limit the scope of this disclosure.

What is claimed is:

1. A system for facilitating communication among grow pods comprising:
   a remote computing device that includes a memory component that stores logic that, when executed by the remote computing device, performs at least the following:
   receive a grow recipe, the grow recipe including actions for a particular grow pod to grow a plant;
   implement the grow recipe on the particular grow pod;
   determine an output of the plant in the particular grow pod using the grow recipe;
   determine a random adjustment to the grow recipe;
   determine an output of the plant in the particular grow pod using the random adjustment to the grow recipe;
   determine whether the random adjustment to the grow recipe resulted in an improvement in output;
   in response to determining that the random adjustment to the grow recipe resulted in an improvement in output, determine a different grow pod for receiving the random adjustment and the grow recipe;
   determine features of the different grow pod;
   alter the grow recipe with the random adjustment to the grow recipe to form a new grow recipe to operate on the different grow pod; and
   implement the new grow recipe on the different grow pod.

2. The system of claim 1 further comprising:
   the particular grow pod, wherein the particular grow pod comprises:
   a first pod computing device; and
   a plurality of environment affecters,
   wherein the random adjustment to the grow recipe relates to at least one of the plurality of environment affecters.

3. The system of claim 1, wherein the logic causes the remote computing device to perform at least the following:
   in response to determining that the random adjustment to the grow recipe did not result in an improvement in output, store the random adjustment to the grow recipe.

4. The system of claim 3, wherein the logic further causes the remote computing device to perform at least the following:
   compare the random adjustment to the grow recipe to a previously-stored random adjustment to the grow recipe that did not result in an improvement in output of the plant;
   in response to determining that the random adjustment to the grow recipe is similar to the previously-stored random adjustment to the grow recipe, discard the random adjustment to the grow recipe; and
   identify another random adjustment to the grow recipe.

5. The system of claim 1, further comprising:
   a second pod computing device for the different grow pod, the second pod computing device coupled to the remote computing device, wherein the second pod computing device performs at least the following:
   receive the new grow recipe;
   determine if the new grow recipe is formatted for the different grow pod; and
   in response to determining that the new grow recipe is not formatted for the different grow pod, further alter the new grow recipe to operate on the different grow pod.

6. The system of claim 1, wherein the random adjustment to the grow recipe includes altering an amount of at least one of the following provided to the plant: air, water, light, airflow, temperature, pressure, or nutrients.

7. The system of claim 1, wherein determining an output of the plant relates to at least one of the following: root growth, stem growth, chlorophyll growth, leaf growth, or fruit output.

8. The system of claim 1, wherein determining whether the random adjustment to the grow recipe resulted in an improvement in output further comprises:
   comparing a predetermined growth profile that includes a desired output for a plurality of growth factors of the plant with the output of the plant in the particular grow pod using the random adjustment to the grow recipe.

9. A method for facilitating communication among grow pods comprising:
   receiving a grow recipe, the grow recipe including actions for a particular grow pod to grow a plant;
   implementing the grow recipe on the particular grow pod;
   determining an output of the plant in the particular grow pod using the grow recipe;
   determining a random adjustment to the grow recipe;
   determining an output of the plant in the particular grow pod using the random adjustment to the grow recipe;
   determining whether the random adjustment to the grow recipe resulted in an improvement in output;
   in response to determining that the random adjustment to the grow recipe did not result in an improvement in output, storing the random adjustment to the grow recipe;

in response to determining that the random adjustment to the grow recipe resulted in an improvement in output, determining a different grow pod for receiving the random adjustment and the grow recipe;

determining features of the different grow pod;

altering the grow recipe with the random adjustment to the grow recipe to form a new grow recipe to operate on the different grow pod; and sending the new grow recipe to the different grow pod for implementation.

10. The method of claim 9, wherein:

the particular grow pod includes a plurality of environment affecters, and the random adjustment to the grow recipe relates to at least one of the plurality of environment affecters.

11. The method of claim 9 further comprising:

comparing the random adjustment to the grow recipe to a previously-stored random adjustment to the grow recipe that did not result in an improvement in output of the plant;

in response to determining that the random adjustment to the grow recipe is similar to the previously-stored random adjustment to the grow recipe, discarding the random adjustment to the grow recipe; and identifying another random adjustment to the grow recipe.

12. The method of claim 9, further comprising:

receiving the new grow recipe;

determining if the new grow recipe is formatted for the different grow pod; and in response to determining that the new grow recipe is not formatted for the different grow pod, further altering the new grow recipe to operate on the different grow pod.

13. The method of claim 9, wherein the random adjustment to the grow recipe includes altering an amount of at least one of the following provided to the plant: air, water, light, airflow, temperature, pressure, or nutrients.

14. A grow pod for facilitating communication with other grow pods comprising:

a pod computing device that includes a memory component that stores logic that, when executed by the pod computing device, performs at least the following:

receive a grow recipe, the grow recipe including actions for the grow pod to grow a plant;

implement the grow recipe on the grow pod;

determine an output of the plant in the grow pod using the grow recipe;

determine a random adjustment the grow recipe;

determine an output of the plant in the grow pod using the random adjustment to the grow recipe; and determine whether the random adjustment to the grow recipe resulted in an improvement in output.

15. The grow pod of claim 14, wherein the logic further causes the pod computing device to perform at least the following:

in response to determining that the random adjustment to the grow recipe did not result in an improvement in output, store the random adjustment to the grow recipe.

16. The grow pod of claim 15, wherein the logic further causes the pod computing device to perform at least the following:

compare the random adjustment to the grow recipe to a previously-stored random adjustment to the grow recipe that did not result in an improvement in output of the plant;

in response to determining that the random adjustment to the grow recipe is similar to the previously-stored random adjustment to the grow recipe, discard the random adjustment to the grow recipe; and identify another random adjustment to the grow recipe.

17. The grow pod of claim 14, wherein the logic further causes the grow pod to perform at least the following:

in response to determining that the random adjustment to the grow recipe resulted in an improvement in output, send the grow recipe and the random adjustment to the grow recipe to a remote computing device, wherein the remote computing device determines a different grow pod with at least one different feature for receiving the random adjustment and the grow recipe.

18. The grow pod of claim 14, wherein the logic further causes the grow pod to perform at least the following:

in response to determining that the random adjustment to the grow recipe resulted in an improvement in output, determine a different grow pod for receiving the random adjustment and the grow recipe;

determine features of the different grow pod;

alter the grow recipe with the random adjustment to the grow recipe to form a new grow recipe to operate on the different grow pod; and send the new grow recipe to the different grow pod for implementation.

19. The grow pod of claim 14, wherein determining an output of the plant relates to at least one of the following: root growth, stem growth, chlorophyll growth, leaf growth, or fruit output.

20. The grow pod of claim 14, wherein the random adjustment to the grow recipe includes altering an amount of at least one of the following provided to the plant: air, water, light, airflow, temperature, pressure, or nutrients.

* * * * *